(12) United States Patent
Howard et al.

(10) Patent No.: US 12,097,022 B2
(45) Date of Patent: Sep. 24, 2024

(54) CRANIAL MIDLINE MARKING DEVICE AND METHOD OF USING

(71) Applicant: UNIVERSITY OF IOWA RESEARCH FOUNDATION, Iowa City, IA (US)

(72) Inventors: Matthew A. Howard, Iowa City, IA (US); Michael J. Wardenburg, Iowa City, IA (US); Oliver Elias Flouty, Iowa City, IA (US); Marshall T. Holland, Iowa City, IA (US); Yasunori Nagahama, Iowa City, IA (US); Mario Zanaty, Iowa City, IA (US); Aaron Boes, Iowa City, IA (US); Nicholas Trapp, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 647 days.

(21) Appl. No.: 17/250,930

(22) PCT Filed: Sep. 27, 2019

(86) PCT No.: PCT/US2019/053358
§ 371 (c)(1),
(2) Date: Mar. 29, 2021

(87) PCT Pub. No.: WO2020/069257
PCT Pub. Date: Apr. 2, 2020

(65) Prior Publication Data
US 2021/0338106 A1 Nov. 4, 2021

Related U.S. Application Data

(60) Provisional application No. 62/737,137, filed on Sep. 27, 2018.

(51) Int. Cl.
A61B 5/107 (2006.01)
(52) U.S. Cl.
CPC ................................. A61B 5/1075 (2013.01)
(58) Field of Classification Search
CPC .................................................... A61B 5/1075
See application file for complete search history.

(56) References Cited

U.S. PATENT DOCUMENTS

| 2,494,792 A * | 1/1950 | Bloom | A61B 90/14 33/512 |
|---|---|---|---|
| 3,713,329 A | 1/1973 | Munger | |

(Continued)

FOREIGN PATENT DOCUMENTS

| CN | 203915075 U | 11/2014 |
|---|---|---|
| CN | 107714085 A | 2/2018 |
| CN | 114711985 A * | 7/2022 |

OTHER PUBLICATIONS

Malinger et al., "Fetal brain imaging: a comparison between magnetic resonance imaging and dedicated neurosonography", Ultrasound Obstet Gynecol, vol. 23, pp. 333-340, 2004.

(Continued)

*Primary Examiner* — Yaritza Guadalupe-McCall
(74) *Attorney, Agent, or Firm* — McKee, Voorhees & Sease, PLC (57) ABSTRACT

A caliper type device is provided for identifying the cranial midline on a patient. The device includes a pair of arms have first ends for receipt in a patients ears, and opposite, pivotally connected second ends which allow the arms to open and close to fit to different sized heads of various patients. A housing at the second end of the arms holds a laser pointer or other tool for identifying the cranial midline after the device is positioned on the patients head.

15 Claims, 5 Drawing Sheets

(56) References Cited

U.S. PATENT DOCUMENTS

| | | | | |
|---|---|---|---|---|
| 4,084,319 A * | 4/1978 | Dragan | A61C 19/045 | 433/73 |
| 4,226,025 A * | 10/1980 | Wheeler | G01B 3/166 | 600/587 |
| 4,639,220 A * | 1/1987 | Nara | A61C 19/045 | 433/68 |
| 4,896,679 A * | 1/1990 | St. Pierre | A61F 11/10 | 128/868 |
| 5,094,241 A | 3/1992 | Allen | | |
| 5,154,003 A * | 10/1992 | Moore | G01B 7/12 | 33/798 |
| 5,176,689 A | 1/1993 | Hardy et al. | | |
| 5,203,091 A * | 4/1993 | Al-Farsy | G01B 3/166 | 33/DIG. 1 |
| 5,222,499 A | 6/1993 | Allen et al. | | |
| 5,330,485 A * | 7/1994 | Clayman | A61B 90/11 | 606/1 |
| 5,398,577 A * | 3/1995 | Pierce | A01G 23/099 | 144/380 |
| 5,473,940 A * | 12/1995 | Parker | G01B 3/166 | 73/487 |
| 5,788,713 A | 8/1998 | Dubach et al. | | |
| 6,096,048 A * | 8/2000 | Howard, III | A61B 90/10 | 600/417 |
| 6,132,437 A | 10/2000 | Omurtag et al. | | |
| 6,152,732 A * | 11/2000 | Lindekugel | A61C 19/045 | 433/73 |
| 6,564,463 B1 * | 5/2003 | Panz | A61B 5/107 | 132/214 |
| 6,726,479 B2 * | 4/2004 | Tremont | A61C 19/045 | 33/513 |
| 7,122,038 B2 * | 10/2006 | Thomas | A61B 90/11 | 606/130 |
| 7,231,723 B1 * | 6/2007 | O'Neill | A61B 5/6835 | 33/511 |
| 7,335,167 B1 * | 2/2008 | Mummy | A61B 5/1071 | 600/595 |
| 8,127,459 B2 * | 3/2012 | Nunes | A61B 5/1076 | 33/514 |
| 8,505,121 B2 * | 8/2013 | Ahlgren | A42B 3/145 | 2/418 |
| 8,827,933 B2 * | 9/2014 | Lang | A61C 19/045 | 33/513 |
| 2002/0046471 A1 * | 4/2002 | Skidmore | G01G 17/08 | 33/511 |
| 2005/0124919 A1 * | 6/2005 | Castillo | A61B 5/1077 | 600/595 |
| 2008/0033321 A1 * | 2/2008 | Hahn | A61B 5/103 | 600/587 |
| 2012/0017547 A1 * | 1/2012 | Rieser | A61B 5/4561 | 54/44.1 |
| 2016/0374593 A1 * | 12/2016 | Martin | A61B 5/0053 | 600/587 |
| 2020/0170682 A1 * | 6/2020 | Boehm, Jr. | A61B 17/7005 | |
| 2021/0338106 A1 * | 11/2021 | Howard | A61B 5/1075 | |

OTHER PUBLICATIONS

White, D N Professor, "Clinical Evaluation of Accuracy of Automatic Measurement of Cerebral Midline", Proc. roy. Soc. Med., vol. 67, 1 page, Feb. 1974.

Woerdeman et al., "Application accuracy in frameless image-guided neurosurgery: a comparison study of three patient-to-image registration methods", J Neurosurg, vol. 106, pp. 1012-1016, 2007.

* cited by examiner

CRANIAL MIDLINE MARKING DEVICE AND METHOD OF USING

CROSS-REFERENCE TO RELATED APPLICATIONS

This application claims priority to Provisional Application U.S. Ser. No. 62/737,137, filed on Sep. 27, 2018, which is herein incorporated by reference in its entirety.

BACKGROUND OF THE INVENTION

Identifying key anatomical landmarks such as the midline of the head and maintaining orientation is critical to any successful surgery. While this is fairly simple when performing surgeries in the anterior region of the head with reliable landmarks such as the nose and ears, maintaining precise orientation becomes far more difficult when performing surgical interventions in the posterior portion of the head. When the surgeon views the patient's head from a posterior perspective orienting landmarks, such as the ears or contour of the skull can be obscured by the patient's hair, leading to errors in estimating the posterior midline.

Accurate identification of the cranial midline is also key in targeting techniques that use repetitive TMS, such as beam F3 method used for depression treatment. Use of the device 10 can improve the accuracy of scalp measurements associated with target localization for repetitive TMS treatment protocols. Repetitive transcranial magnetic stimulation (TMS) is an FDA-approved treatment for major depressive disorder when targeted at the left prefrontal cortex [1]. However, the optimal cortical target within the left prefrontal cortex and the ideal method for identifying the target are unclear. One of the most commonly used targeting methods, Beam F3, utilizes scalp landmarks to identify a left prefrontal brain region that corresponds with the F3 location of a 10-20 EEG measurement system. The reliability of target identification with Beam F3 requires accurate identification of the cranial midline at the inion of the skull and the cranial vertex. To date, little research exists to examine the reliability and reproducibility of identification of these cranial midline targets, though the introduction of any error in these measurements would compromise successful target localization.

Complicated solutions to this cranial midline identification problem have been proposed which involve imaging and positioning patients using intricate devices. Additionally, the solutions consume medical staff time that is costly and depending upon the status of the patient, detrimental to the health of the patient.

Devices for measuring the head have also been designed. These devices, however, fail to accurately, easily, and systematically identify geographic points on the head.

Therefore, it is a principal object, feature, and/or advantage of the disclosed features to overcome the deficiencies in the art.

Another objective, feature, and/or advantage of the present invention is the provision of a cranial midline marking device in the form of a caliper for marking the midline.

A further objective, feature, and/or advantage of the present invention is a provision of a cranial midline marking device which can be adjusted to fit various sized heads.

Still another objective, feature, and/or advantage of the present invention is the provision of a method for identifying the cranial midline on a patient's head using a caliper type device with a pair of curved arms having terminal ends adapted to be received in the patient's ears.

These and/or other objects, features, and advantages of the disclosure will be apparent to those skilled in the art. The present invention is not to be limited to or by these objects, features and advantages. No single embodiment need provide each and every object, feature, or advantage.

SUMMARY OF THE INVENTION

The invention is directed toward a device and method for cranial midline identification and marking on the head of a subject. This midline marking device is adjustable so as to be usable on a variety of head sizes and head shapes. The device can be adjusted easily while maintaining the ability of the sighting mechanism to always point down the centerline between a pair of caliper arms.

The device has a U-shape, similar to a horseshoe or wishbone. The device is adjustable to head size, with "calipers" arms that anchor in the bilateral external auditory canals with metallic spheres. A laser sight is located at the top of the device with a sighting mechanism to ensure the laser consistently illuminates the midpoint between the two metallic spheres. The device can swivel around its anchor point in the auditory canals, allowing identification of midline targets at any point along the mid-sagittal plane.

In a preferred embodiment, the midline marking device includes a left auditory canal insert or sphere and a right auditory canal insert or sphere, a left caliper arm and a right caliper arm, a left caliper alignment arm and a right caliper alignment arm, a midline sighting housing having a caliper arm joint position and an oblong opening or slot for receiving a left and right caliper alignment arm joint, wherein the left auditory canal insert is connected to the left caliper arm and the right auditory canal insert is connected to the right caliper arm, and the right and left caliper arms are connected to the midline sighting housing at a caliper arm joint and wherein the left caliper alignment arm is connected to the left caliper arm at the left alignment arm joint and the right caliper alignment arm is connected to the right caliper arm at the right alignment arm joint; and a sighting mechanism mounted along the midline sighting housing wherein the sighting mechanism is capable of identifying the midline of a head.

In other embodiments, the sighting mechanism can include a tattoo pen, pencil, pen, marker, chalk or the like. In a preferred embodiment, the sighting mechanism is a laser pointer.

Preferably, the device is symmetrical along a longitudinal axis, with the caliper arms having opposite, mirrored curvatures. The shape of the caliper arms and caliper alignment arms do not necessarily need to be the same. Rather the arms simply need to function to maintain the geometry described below.

The invention also includes methods of using the device. For example, the methods can include an initial step of positioning the device such that it snuggly fits in the ears and then ensuring symmetry by focusing the sighting mechanism on a facial feature, such as the lips, nose, chin, or eyebrow midpoint. The device can be then rotated around to the posterior of the head while maintaining the auditory canal insert in place and the midline can be identified. Moreover, a midline point anywhere along the head, ranging from the face to the posterior base of the head can be identified.

These and other aspects of the invention will be appreciated upon review of the figures, description and claims.

DETAILED DESCRIPTION OF THE PREFERRED EMBODIMENTS

Figure 1:
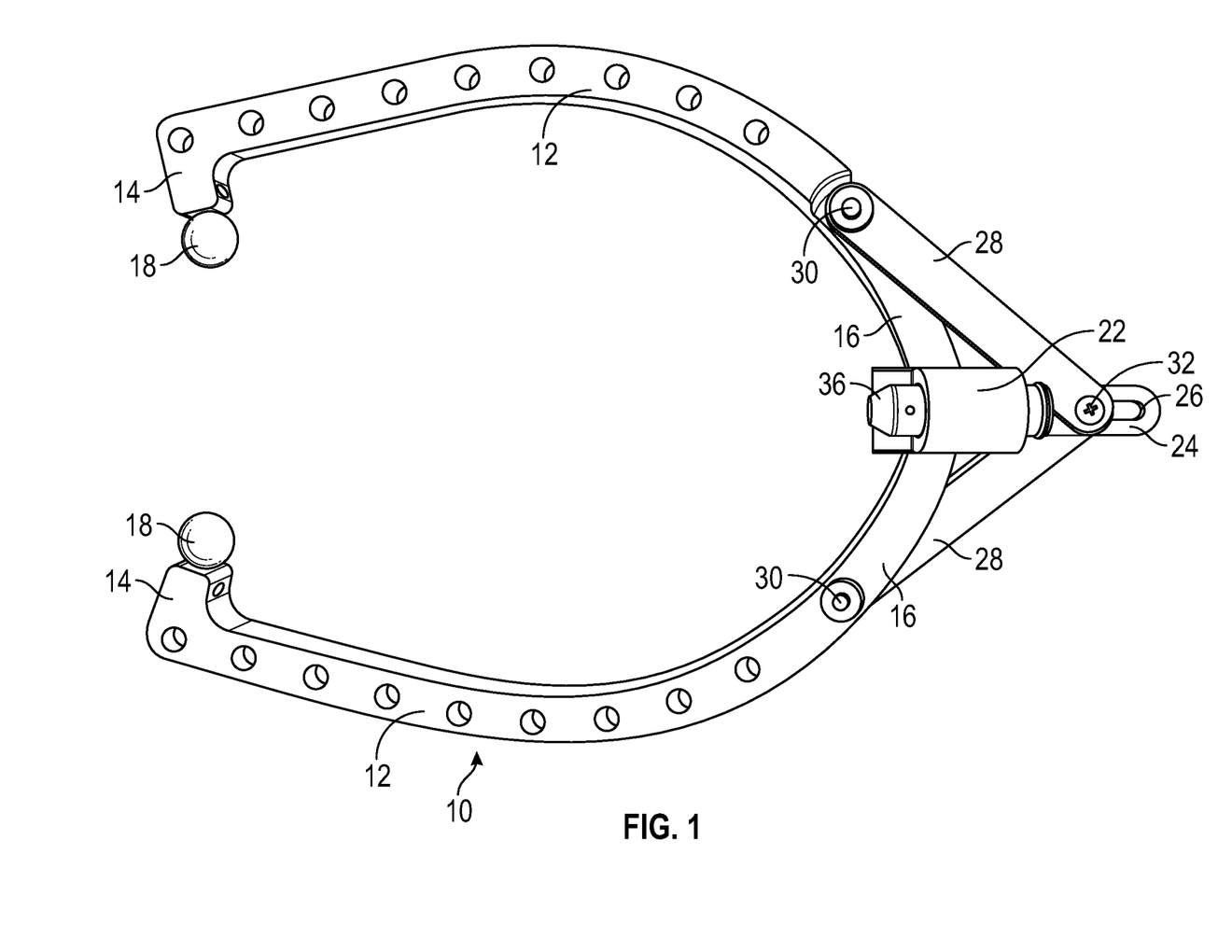
FIG. 1 is a top plan view of a one embodiment of the midline marking device (MMD) of the present invention in a closed position.
Figure 2:
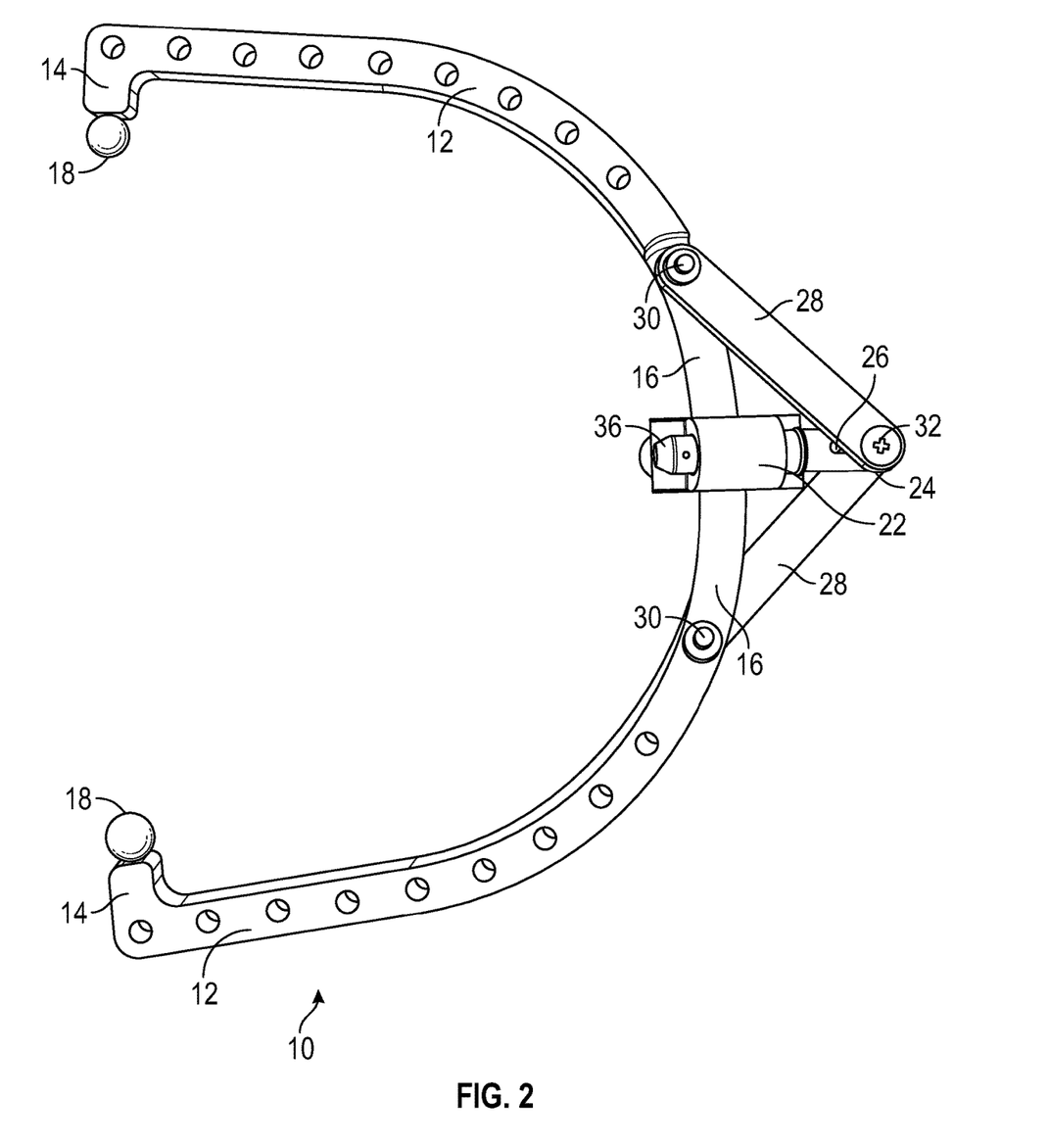
FIG. 2 is a top plan view of the MMD in an open position.
Figure 3:
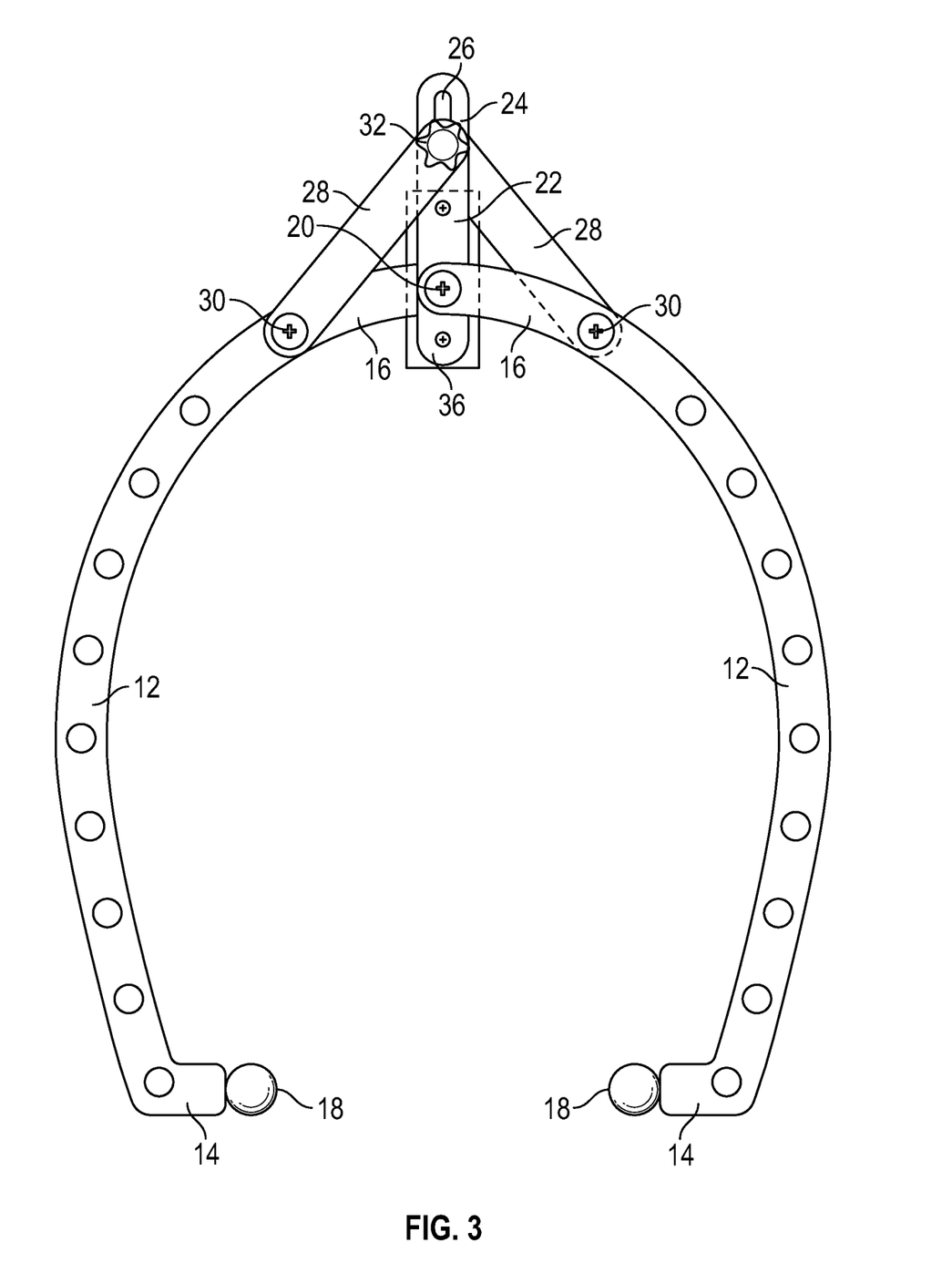
FIG. 3 is a bottom plan view of the MMD in a closed position.
Figure 4:
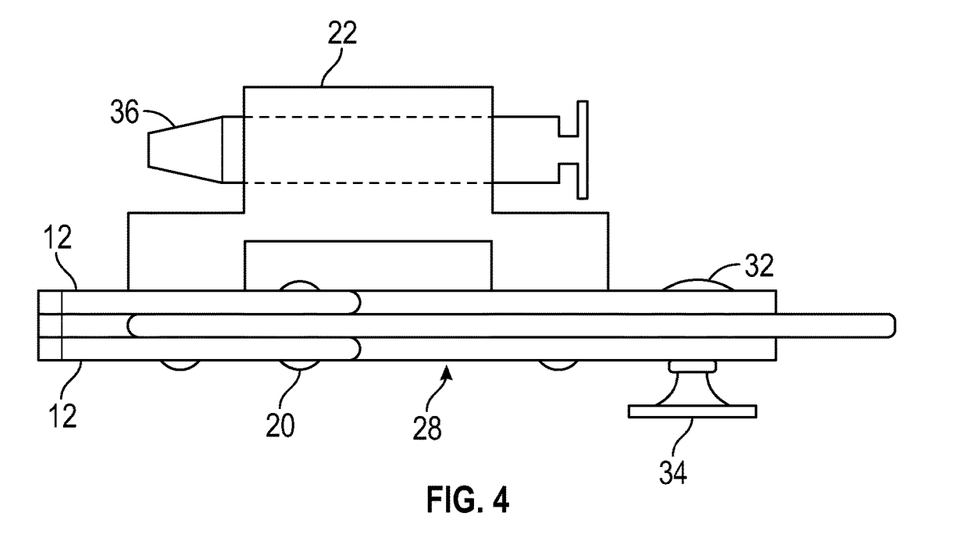
FIG. 4 is a side elevation view of the MMD in a closed position.
Figure 5:
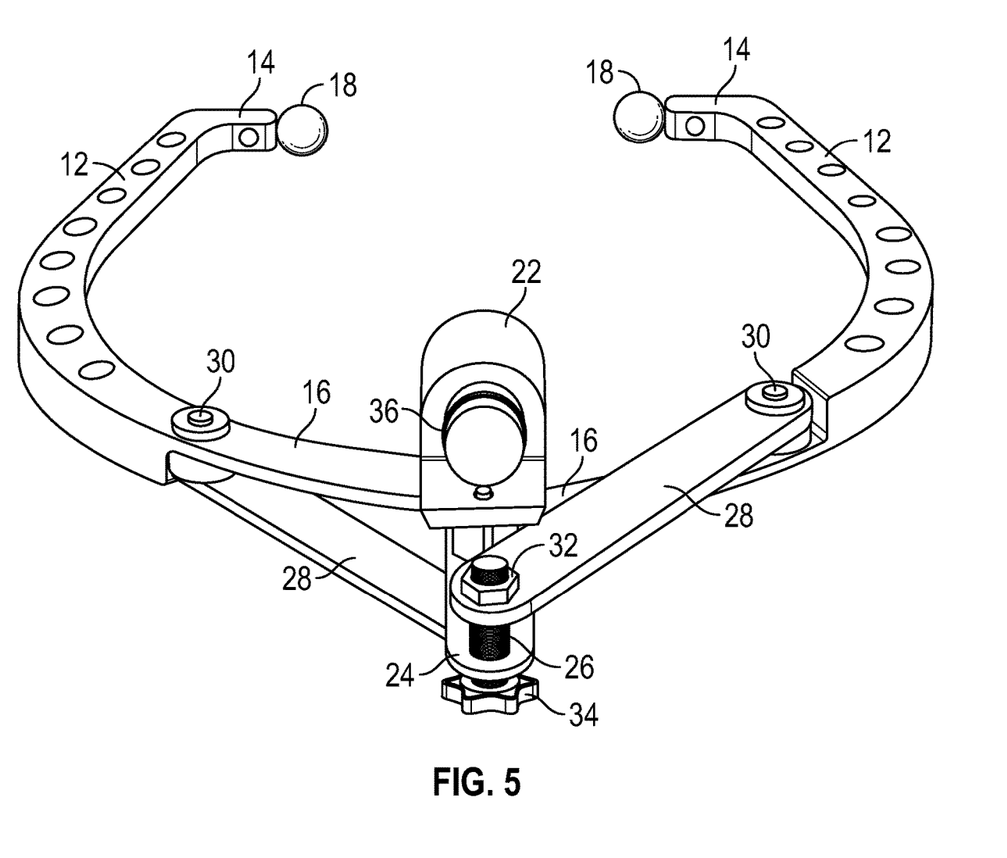
FIG. 5 is a rear perspective view of the MMD in a closed position.

The cranial midline marking device of the present invention is generally designated in the drawings by the reference numeral 10. The device includes a pair of curved arms 12 having spaced apart first ends 14 and pivotally connected second ends 16. Soft cushions or spheres 18 are mounted on the ends 14 of the arms and may be replaceable and disposable for sanitary purposes. A pivot pin, rivet, or bolt 20 secures the second ends 16 together. A housing 22 is mounted to the arms 12 adjacent the second ends 16 and includes a rearwardly extending leg 24 with a slot 26 therein. First and second adjustment arms 28 each have one end pivotally connected to the left and right arms 12 by a pivot pin, rivet, or bolt 30. The adjustment arms 28 are pivotally connected by a pin, rivet or bolt 34 which also extends through the slot 26 in the leg 24 of the housing 22. The adjustment arms caliper arms 12 can be moved via the adjustment arms 28 to open and closed positions, as shown in FIGS. 1 and 2, respectively, such that the device 10 can be fit on various sized heads of different patients. A knob or thumb screw 34 can be loosened to open and close the arms 12 and can be tightened to fix the arms 12 in a desired position. The housing 22 includes a longitudinal bore in which is secured a marker or sighting mechanism 36, such as a laser pointer. The laser pointer 36 is adapted to emit a laser beam 38.

In use, the knob 34 is loosened, and the caliper arms 12 are opened so that the spheres 18 can be positioned in each of the canals of the patient's ears. The knob 34 is then tightened to hold the arms 12 in a set position. The laser pointer 34 is activated. Then the device 10 is gently moved forwardly and rearwardly while the spherical inserts 18 remain in the patient's ears, such that the laser beam 38 automatically locates the midline on the patient's skull. The beam 28 can be traced with a marking pen or other tool so as to place a line on the patient's skull corresponding to the skull midline. A secondary laser pointer (not shown) may also be utilized on the device 10 to further assist in F3 localization.

The MMD basic design is similar to a caliper (FIGS. 1 and 2) and utilizes the patient's left and right external auditory canals (EAC) as standard landmarks. Soft stainless steel external auditory canal spheres are gently positioned within the bilateral EACs. The midline is indicated by a laser pointer that always points to the midpoint between the exits of the two EACs. The sighting mechanism or marker 36 at the posterior end of the device always points to and aligns with the midpoint between the two EAC spheres. Similar to a caliper, the MMD can be adjusted for all different head sizes. The housing 22 of the MMD allows the marker 36 to be directed at the midline at all times, independent of the arm positions.

Figure 6A:
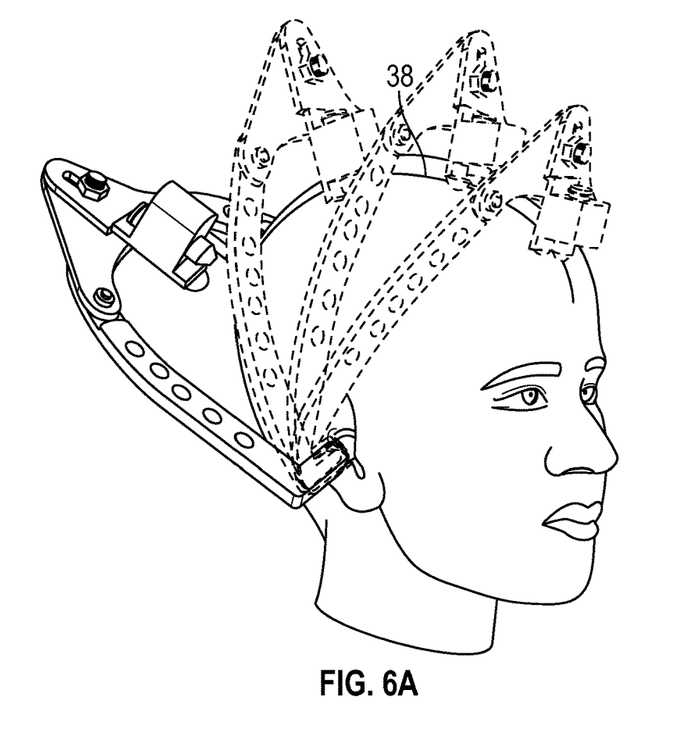
FIGS. 6A and 6B are views of the device positioned for use on a person.
Figure 6B:
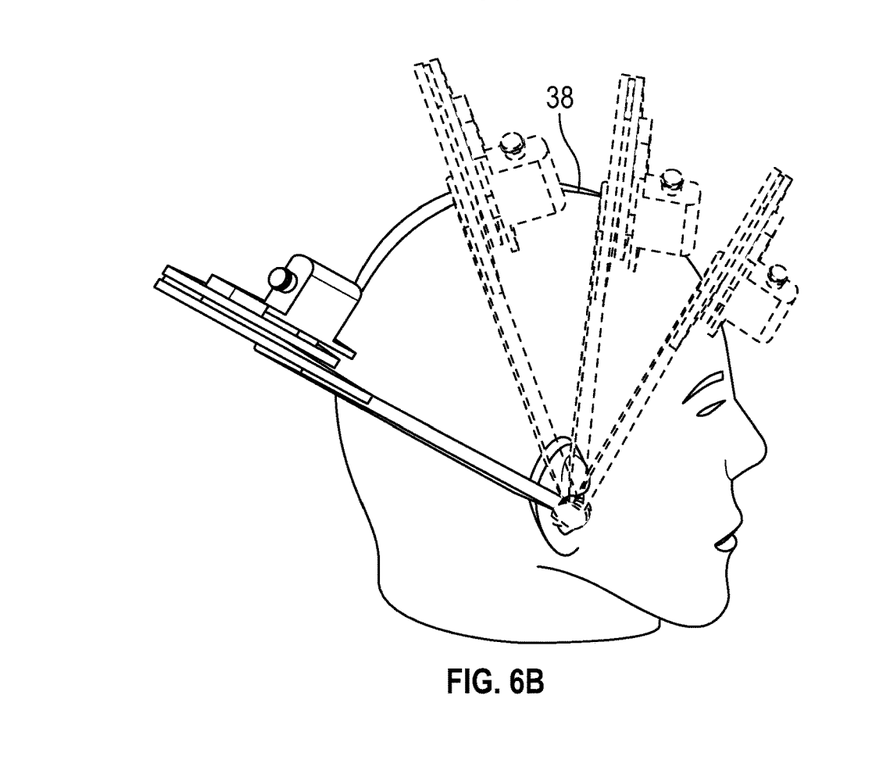

One intended use of device 10 is in a cranial operation. After patients are placed under general anesthesia, during the pre-procedure planning phase, the MMD will be utilized. The MMD arms will be positioned with the spheres placed into the bilateral EACs. After being secured in place by tightening the adjustment knob the laser pointer is turned on which identifies the midline, as shown in FIGS. 6A and 6B. The midline can then be appropriately marked with a surgical marking pen and measurements can be made from this accurate mark. The MMD is then removed from the patient and the surgery can proceed in the usual fashion. This procedure typically will take approximately 5-10 minutes, the same amount of time or less than it typically takes to mark out the midline with anatomical landmark visualization.

Another use of the device 10 is for transcranial magnetic stimulation (TMS). The process is similar to the surgical midline marking technique, though without anesthesia.

One particular advantage of using the MMD is that the laser 36 will always point toward the midpoint between the two external auditory canal spheres. Once the two caliper arms 12 are adjusted so that the external auditory canal spheres 18 rest gently within the bilateral external auditory canals of the patient, the midpoint between these two spheres will represent the midpoint of the head along the sagittal plane. This allows accurate marking of the midline and precise measurements off the midline to be made. The use of the MMD 10 does not rely on the palpation of the inion or direct visualization of the eyes or nose, which can be difficult in patients in the prone position. Furthermore, as the laser continues to point to the midline 38, the patient's hair can be moved out of the way and the midline marked, thus avoiding possible distortion from copious amounts of hair that may occur when using a straight edge marker.

With reference to the Figures, a triangle geometry is created through the joining of the left and right sliding caliper alignment arms at the vertex, the joining of the right and left sliding caliper alignment arms to their respective joints and the joining of the caliper arms at the caliper arm joint. The midline sighting housing then bisects the triangle created by these joints. The midline marking device includes any combinations of joinery along the midline sighting housing that allow the movement of the caliper arm joint and/or the left and right caliper alignment arm joint to flex and open and close the caliper arms. For example, the caliper arm joint can be positioned in an oblong opening and the left and right sliding caliper alignment arm joint can be located at a fixed position along the midline sighting housing.

The joints described herein can be made of any structure that allows the caliper arms and/or alignment arms to be joined in a hinged fashion. For example, bolts, rivets and the like can be used. Moreover, the joints do not necessarily need to use the same structure. For example, a rivet can be used at the vertex and a bolt can be used at the caliper arm joint as long as the functionality is maintained.

The midline marking device can be made of any material that is capable of creating a rigid shape and that can be sufficiently cleaned for use in an operating room setting. For example, the calipers and caliper arms can be made of polystyrenes, polycarbonates, steel, aluminum and the like. Moreover, the device does not need to be made from 100% the same material. For example, the auditory canal inserts can be made of soft steel, semi-ridged polymers and the like allowing for a snug fit in the canal, while the remainder of the device can be made from aluminum. In one embodiment, the auditory canal inserts can be disposable.

If desired, disposable covers can be provide on the spheres 18 to eliminate the need to clean the spheres after use of the device 10.

Test Example #1

While the patient's head is positioned flat on the bed, the midline marking device 10 (MMD) adjusted by first adjusting the caliper arms 12 and the two external auditory canal spheres 18 are firmly positioned within the left and right external auditory canals of the patient. Once the adjustment knob 34 is tightened, the caliper arms 12 are locked in position and the device 10 is secured to the patient's skull. Initially, the device 10 is rotated so that the laser beam 38 is directed at the forehead just above the nose, ensuring proper insertion of the earpieces 18. If the laser beam 38 illuminates the skin in the midline immediately above the nose, this indicates that the MMD 10 has been appropriately deployed. Next, an assistant flexes the patient's head and neck so that the surgeon can visualize the patient's posterior scalp. The device 10 is rotated posteriorly so that the laser pointer 36 illuminates the posterior midline. The surgeon uses a scalp marker to trace the posterior midline as delineated by the laser 36.

The time was recorded from initial placement of the device 10 until the midline surface was marked in 30 patient-subjects. Staples placed over the identified midline were used as radiographic markers to help calculate the accuracy of the estimated midline. The distance d was calculated in millimeters by measuring the distance between the staples and true midline landmarks seen on postoperative CT scan, such as the sagittal sinus and the falx cerebri. Accuracy was calculated by measuring the arithmetic mean of d collected over 30 patient-subjects. The staples were removed on postoperative day one following the CT scan.

Thirty consecutive patient-subjects underwent placement of a parietal approach VPS. No complications were noted. Data collected from this group demonstrates that the MMD is easy to master and requires less than approximately three minutes to delineate the posterior midline. The MMD localized the posterior midline consistently and in a comparable fashion to that reported using surface tracing-based frameless stereotaxis methods. The cost of the MMD is less than 1% of that of a frameless stereotactic system.

Test Example #2

For the purposes of this study, the device was used to plot points at the midline vertex and inion/occiput of the head of multiples subjects.

A T1-weighted structural MRI was obtained on a 7T GE MR950 scanner within 30 days of participation. Images were resampled to 1 mm isotropic voxels and the intensity range was truncated to standardize values from air-to-scalp-to-skull. The processed images were loaded into Brainsight neuronavigation equipment (Rogue Research, Montreal, Quebec) for measurement.

Three trained TMS technicians performed repeated scalp measurements on each of the 5 subjects at various time points over the course of one month (n=54 measurements, 27 at each of two targets; 6 to 18 measurements per subject). Two targets were investigated: 1) the vertex compared to the falx cerebri midline on MRI, and 2) the inion/midline occiput compared to an MRI-defined midline occiput. This MRI occiput was identified by a posterior point in the mid-sagittal plane that bisected the falx cerebri, third ventricle, and cerebral aqueduct. A second sample including only vertex measurements was also analyzed (3 technicians×3 time points=9 measurements per subject×7 subjects=63 measurements−1 lost data point=62 measurements). Technicians used visual inspection, palpation of scalp landmarks, and tape measurement according to standard clinical practices to identify the two midline targets in each subject, as required for Beam F3 targeting. The midline landmarks were marked on a Lycra cap worn by the subject and immediately plotted onto the patient's brain MRI using Brainsight. Technician measurements were compared to the midline identified by the MMD "wishbone" 10, and both were compared to a "gold standard" MRI-defined midline. The two main analyses focused on 1) whether the MMD 10 resulted in less distance from the midline compared to technician measurements, evaluated using a T-test, and 2) whether there was a higher proportion of measurements within a predefined 5 mm margin of error using the MMD 10, evaluated with a Chi-square test. Standard figure-8 TMS coils are thought to stimulate a brain region on the order of 1-2 $cm^2$, so cumulative error >5 mm was selected as a threshold for stimulating unwanted or unexpected brain structures.

Across all recorded measurements the MMD 10 was significantly more accurate in identifying the midline compared to technician-based measurements (n=54; 2.94+/−2.64 mm versus 5.34+/−4.74 mm, p=0.00025). This difference was significant when analyzing results from the vertex or inion independently (see online supplemental Table 1, p=0.003 and p=0.008, respectively). The device 10 outperformed the technician measurements with 78% accuracy within 5 mm of the actual midline compared to 54% for technician measurements (p=0.008, chi square)–see supplemental Table 2 for details, along with proportional accuracy as defined by 1 mm or 10 mm. Notably, use of the device 10 to confirm or correct midline vertex and occiput targets added less than 15 seconds of technician time per patient and would have resulted in >5 mm corrections of technician targeting 20% of the time (including 37% of inion measurements).

This data highlights the challenges with reliable target identification by TMS technicians utilizing the Beam F3 method. The vertex and inion are especially critical landmarks that serve as guide-points for later measurements (e.g. nasion-to-inion distance) and directly impact the accuracy of the final stimulation site. While no evidence to date confirms that more precise or reliable targeting of TMS therapy results in better outcomes for patients, it remains important to know where one is stimulating, and to reliably stimulate the target intended by the targeting method to enable valid scientific inquiry and further optimization of treatment parameters. The data in this report demonstrates that use of a laser-sighted midline localizer device 10, efficiently identifies the scalp midline at the vertex and inion with a greater degree of accuracy than technician-identified landmarks. As such, the device 10 incorporated into the Beam F3 targeting procedure is a quality control measure that minimizes error in identifying midline structures. This will help ensure the successful identification of a reliable and valid F3 target for repetitive TMS treatment protocols for depression therapy.

TABLE 1

Differences between "wishbone" midline targeting and technician midline targeting. Mean differences between the vertex and midline occiput as identified by the "wishbone" and those as identified by a technician compared to a structural MRI standard. The "wishbone" measurements were significantly more accurate than those obtained by the technician. All data analyzed from initial sample (n = 27), although replication sample values show similar results within 0.1 mm at vertex.

| Measurement | Mean Difference (mm) | Standard Deviation (mm) | P-value |
|---|---|---|---|
| Wishbone Vertex to Falx Cerebri | 2.45 | 2.34 | 0.003 |
| Technician Vertex to Falx Cerebri | 4.07 | 3.48 | |
| Wishbone Occiput to MRI Occiput | 3.43 | 2.86 | 0.008 |
| Technician Occiput to MRI Occiput | 6.61 | 5.51 | |

TABLE 2

"Wishbone" targeting. Precision for midline vertex and occiput identification as assessed by the percentage of total measurements which came within 1 mm, 5 mm, and 10 mm of the neuronavigation-confirmed midline, respectively. All data are from the initial sample (n = 54) unless otherwise noted.

| Target (& Targeting Method) | Measurements ≤1 mm off midline (%) | Measurements ≤5 mm off midline (%) | Measurements ≤10 mm off midline (%) |
|---|---|---|---|
| Wishbone Vertex (compared to Falx Cerebri) | 37.0% | 81.5% | 100% |
| Wishbone Vertex (compared to Falx Cerebri) - Replication sample (n = 62) | 45.2% | 85.5% | 100% |
| Technician Vertex (compared to Falx Cerebri) | 25.9% | 59.3% | 96.3% |
| Wishbone Occiput (compared to MRI midline) | 25.9% | 74.1% | 100% |
| Technician Occiput (compared to MRI midline) | 3.7% | 48.1% | 77.8% |

The invention has been shown and described above with the preferred embodiments, and it is understood that many modifications, substitutions, and additional may be made which are within the intended spirit and scope of the invention. From the foregoing, it can be appreciated that the present invention accomplishes at least all of its stated objectives.

What is claimed is:

1. A midline marking device, comprising:
   a left auditory canal insert, and a right auditory canal insert;
   a left caliper arm and a right caliper arm;
   a left caliper alignment arm and a right caliper alignment arm;
   a midline sighting housing having a caliper arm joint position and an oblong opening for receiving a left and right caliper alignment arm joint;
   wherein the left auditory canal insert is connected the left caliper arm and the right auditory canal insert is connected to the right caliper arm, and the right and left caliper arms are connected to the midline sighting housing at the caliper arm joint; and
   wherein the left caliper alignment arm is connected to the left caliper arm at the left alignment arm joint and the right caliper alignment arm is connected to the right caliper arm at the right alignment arm joint; and
   a sighting mechanism mounted along the midline sighting housing wherein the sighting mechanism is capable of identifying the midline of a head.

2. The midline marking device according to claim 1, wherein the sighting mechanism is selected from a tattoo pen, pencil, pen, marker, chalk or the like.

3. The midline marking device according to claim 1, wherein the sighting mechanism is a laser pointer.

4. The midline marking device according to claim 1, wherein left caliper alignment arm and the right caliper alignment arm are rigid.

5. The midline marking device according to claim 1, wherein the left caliper alignment arm and the right caliper alignment are the same shape.

6. The midline marking device according to claim 1, wherein the left caliper alignment arm and the right caliper alignment are curved.

7. The midline marking device according to claim 1, wherein each of the left auditory canal insert and the right auditory canal insert is a sphere.

8. A cranial midline marking device, comprising:
   left and right caliper arms each having a first end and a second end, the second ends being pivotally coupled to one another such that the arms are movable between open and closed positions, and the first ends being adapted for insertion into a patient's ears; and
   a marker mounted adjacent the second ends of the caliper arms for identifying the midline of a head when the auditory canal inserts are positioned in a patient's ears; and
   left and right adjustment arms each having first and second ends, with the first ends being pivotally coupled to the left and right caliper arms, respectively, and the second ends being pivotally coupled to one another.

9. The device of claim 8 wherein the caliper arms are curved.

10. The device of claim 8 wherein the marker is a laser pointer.

11. The device of claim 8 further comprising a housing on the caliper arms for holding the marker and including a slot for slidably receiving a coupler on the adjustment arms.

12. The device of claim 11 wherein the housing has a bore to receive the laser pointer.

13. The device of claim 8 wherein the caliper arms form a symmetrical U-shape.

14. The device of claim 8 wherein the caliper arms form a wishbone shape.

15. The device of claim 8 wherein the marker is directed centrally between the arms.

* * * * *